United States Patent [19]

Kaye et al.

[11] 3,947,440

[45] Mar. 30, 1976

[54] MANUFACTURE OF 2-(ALKYL)AMINO-4-HYDROXY-5-ALKYLPYRIMIDINES

[75] Inventors: Albert Edward Kaye; Alan Cyril Tucker, both of Manchester, England

[73] Assignee: Imperial Chemical Industries Limited, London, England

[22] Filed: Jan. 2, 1974

[21] Appl. No.: 429,808

[30] Foreign Application Priority Data

Jan. 4, 1973 United Kingdom.................. 491/73

[52] U.S. Cl.................... 260/256.4 C; 260/256.4 N
[51] Int. Cl.².................................... C07D 239/34
[58] Field of Search... 260/256.4 C, 256.4 N, 296 N

[56] References Cited
UNITED STATES PATENTS 3,428,641    2/1969    Myerly et al.................... 260/296 N

*Primary Examiner*—Richard J. Gallagher
*Assistant Examiner*—James H. Turnipseed
*Attorney, Agent, or Firm*—Cushman, Darby & Cushman

[57] ABSTRACT

Reaction of a 2-amino-, 2-alkylamino- or 2-dialkylamino-4-hydroxypyrimidine, preferably also containing a methyl group at the 6 position, with an aldehyde R—CHO in presence of hydrogen and a hydrogenation catalyst introduces an alkyl group R—CH$_2$— into the 5 position. The reaction is preferably carried out under superatmospheric pressure at a temperature between 80° and 180°C and is aided by metal salts, acids, amines, amine salts or basic ion-exchange resins.

8 Claims, No Drawings

MANUFACTURE OF 2-(ALKYL)AMINO-4-HYDROXY-5-ALKYL-PYRIMIDINES

This invention relates to a process for the manufacture of pyrimidines and more particularly of 2-amino- and 2-alkylamino-4-hydroxypyrimidines having a 5-alkyl substituent.

2-Amino-, 2-alkylamino- and 2-dialkylamino-4-hydroxy-5-alkyl-pyrimidines are of importance as fungicides and intermediates for insecticides and fungicides. These compounds have hitherto been prepared from alkylguanidines and C-alkylacylacetic esters which are difficult of access. The present invention provides a method for the manufacture of these compounds in good yields utilising intermediates prepared from alkylguanidines and readily available acylacetic esters.

According to the invention there is provided a process for the manufacutre of 2-amino-, 2-alkylamino- or 2-dialkylamino-4-hydroxy-5- (optionally substituted-)alkylpyrimidines which comprises reacting a 2-amino-, 2-alkylamino- or 2-dialkylamino-4-hydroxypyrimidine with an aldehyde of the formula R.CHO wherein R is a hydrogen atom or an optionally substituted alkyl, alkenyl, phenyl or heterocyclic group in presence of hydrogen and a hydrogenation catalyst.

As aldehydes there may be used any aldehyde of the formula R.CHO wherein R is a hydrogen atom or an optionally substituted alkyl, alkenyl, phenyl or heterocyclic group, but particularly suitable aldehydes are formaldehyde and those in which R is an alkyl group containing not more than five carbon atoms, for example acetaldehyde, n-propionaldehyde, n-butyraldehyde and isobutyraldehyde. Other aldehydes which may be used include crotonaldehyde, benzaldehyde, tolualdehyde, furfural and pyridine-3-carboxaldehyde. Precursors of aldehydes, e.g. paraform, trioxane and acetals such as acetaldehyde diethyl acetal may be used instead of the aldehydes if desired.

As hydrogenation catalyst there are mentioned for example Raney nickel and metals such as platinum and palladium alone or supported on a carrier such as carbon or alumina, and other conventional hydrogenation catalysts.

Suitable amounts of catalysts are for example in the case of carbon carring 3% of palladium from 1 to 20%, and preferably from 2 to 10% of the weight of alkylaminohydroxy pyrimidine.

As examples of 2-amino-, 2-alkylamino- and 2-dialkylamino-4-hydroxypyrimidines which may be used in the process of the invention there are preferred those in which the alkyl group or groups, if any, on the amino groups contain not more than six carbon atoms and those in which the 6 positions in the pyrimidine ring is substituted by a methyl group, but others for example with the 6-position unsubstituted or having a phenyl group may also be used. Specific examples of such pyrimidines include 2-amino-, 2-methylamino-, 2-ethylamino-, 2-propylamino- and 2-n-butylamino-4-hydroxy-6-methylpyrimidines, 2-dimethylamino-, 2-diethylamino-, 2-dipropylamino-, and 2-di-n-butylamino-4-hydroxy-6-methylpyrimidines, 2-methylamino-, 2-ethylamino, 2-propylamino-, 2-n-butylamino- and 2-dimethylamino-4-hydroxypyrimidines and the corresponding pyrimidines in which the 6 position has a phenyl group.

Examples of 2-amino-, 2-alkylamino- and 2-dialkylamino-4-hydroxy-5-alkylpyrimidines which may be prepared by the process of the invention include the 5-methyl, 5-ethyl, 5-propyl and 5-n-butyl derivatives of the 2-amino-, 2-alkylamino- and 2-dialkylamino-4-hydroxypyrimidines listed as starting materials above.

It is preferred to carry out the process in presence of a condensation catalyst such as metal salts such as zinc acetate and chloride, magnesium acetate, aluminium acetate, lithium acetate, nickel chloride, nickel acetate thallium acetate, acids such as acetic, formic and sulphuric acids, salts of amines such as piperidine, diethylamine, and pyridine with acids and acidic salts such as ammonium chloride.

The process is preferably carried out in solution in an organic solvent such as acetic acid, alcohols such as ethanol and n-butanol, or other water-soluble solvents such as dioxan, and mixtures of one or more of the above and with water. Water-miscible solvents are preferred, but wataer-immiscible solvents such as ethyl acetate may be used.

The reaction temperatures may be from 80° to 180°C., and preferably from 100° to 140°C. In presence of a condensation catalyst lower temperatures, from 80° to 120°C., are preferred. It is preferred to carry out this process in a pressure-vessel, the hydrogen being added at a pressure of above atmospheric. The reaction may be conveniently be carried out at pressures up to 5 bar, but higher pressures may be used if desired.

The reactants may for example be mixed and stirred in presence of the hydrogen and the temperature then adjusted to the desired reaction temperature but it is preferred to mix the reactants other than the aldehyde and add the hydrogen, previously or subsequently raising the temperature to the reaction temperature, and then to add the aldehyde gradually with stirring. The amount of aldehyde is preferably from 1 to 2 molar proportions of the amount of the pyrimidine. More may be used but may be wasteful of aldehyde while less results in incomplete alkylation.

The product may be isolated from the reaction mixture by any conventional procedure, for example removal of the catalyst by filtration, removal of solvent by distillation under reduced pressure, and precipitation by water. The product may be purified by solution in aqueous sodium hydroxide, removal of any insoluble material by filtration, and regeneration of the product by neutralisation with acid to a pH of about 6–7.

In the case of 2-amino-4-hydroxypyrimidines the products obtained contain small amounts of 2-alkylamino-5-alkyl-4-hydroxypyrimidines derived by reductive alkylation of the 2-amino group, usually together with a little unchanged starting material and its N-alkyl derivative. The relative proportions of these will depend upon the reaction conditions, increase in pressure causing some increase in N-alkylation. Condensation catalysts in general reduce the amount of N-alkylation.

The invention is illustrated but not limited by the following Examples in which all parts and percentages are by weight unless otherwise stated.

EXAMPLE 1

76.5 Parts of 2-dimethylamino-4-hydroxy-6-methylpyrimidine, 10 parts of zinc acetate and 7 parts of a 50% aqueous paste of a 3% palladium on carbon catalyst are stirred in 250 parts of acetic acid and 250 parts of water in a closed container. Hydrogen is then passed into the reaction vessel to a pressure of 3 bar. The temperature is raised to 100°C and 46 parts of butyraldehyde are added over 4 hours maintaining a hydrogen pressure of 3 bar and temperature 98°–100°C. The reaction mixture is stirred under these conditions for 16 hours and then cooled and the palladium on carbon catalyst removed by screening. The filtrates are distilled under reduced pressure to remove water and acetic acid and the residue drowned into 700 parts of water. A white solid separates, which is collected by filtration and dried in a desiccator to yield 63.8 parts of crude 5-butyl-2-dimethylamino-4-hydroxy-6-methyl pyrimidine. The crude product is dissolved in aqueous caustic soda solution and the solution adjusted to pH 6.4 with hydrochloric acid to yield 54 parts of 5-butyl-2-dimethylamino-4-hydroxy-6-methylpyrimidine analysing at 96% strength.

EXAMPLE 2

The procedure of Example 1 is repeated but replacing the zinc acetate by 10 parts of a basic ion-exchange resin commercially available under the trade name Amberlite 1R–45(OH) to yield 54.8 parts of product, analysing at 88% strength.

EXAMPLE 3

The procedure of Example 1 is repeated but replacing the zinc acetate by 1 part of piperidine and reducing the butyraldehyde usage to 41 parts to yield 30.1 parts of product, analysing at 89% strength.

EXAMPLE 4

382.5 Parts of 2-dimethylamino-4-hydroxy-6-methylpyrimidine, 50 parts of zinc acetate and 35 parts of a 50% aqueous paste of a 3% palladium on carbon catalyst are stirred in 2500 parts of acetic acid and 1000 parts of water in a closed container. Hydrogen is then passed into the reaction vessel to a pressure of 3 bar and the temperature is raised to 100°C. 285 parts of 36% formaldehyde diluted with 500 parts of water are added over 6 hours, maintaining a hydrogen pressure of 3 bar and temperature of 98°– 100°C., followed by the addition of 1075 parts of water. The reaction mixture is stirred under these conditions for a further 17 hours, and then cooled and the palladium on carbon catalyst is removed by filtration. The filtrates are distilled under reduced pressure to remove water and acetic acid and to the residue 2500 parts of water and 150 parts of 32% sodium hydroxide solution are added. The suspension is heated to 60°C. and filtered, the filter cake washed with 22 parts of 32% sodium hydroxide solution diluted with 1000 parts of water. The combined filtrates and washes are adjusted to pH 6 with 100 parts of 35% hydrochloric acid and extracted with chloroform. The chloroform is removed by distillation to yield 283 parts of 2-dimethylamino-4,5-dimethyl-6-hydroxypyrimidine, analysing at 95% strength.

EXAMPLE 5

76.5 Parts of 2-dimethylamino-4-hydroxy-6-methylpyrimidine and 7 parts of a 50% aqueous paste of 3% palladium on carbon are stirred in 250 parts of water and 250 parts of acetic acid in a closed container. Hydrogen is passed into the reaction vessel to a pressure of 3 bar and the temperature is raised to 100°C. 57 Parts of 36% w/w formaldehyde containing 1.1 part of piperidine and 2.5 parts of acetic acid are added over 4½ hours, maintaining a hydrogen pressure of 3 bar and the temperature at 100°–102°C. The reaction mixture is stirred under these conditions for a further 6 hours and then cooled and the palladium on carbon catalyst removed by filtration. The filtrates are distilled under pressure to remove water and acetic acid and the residue dissolved in 250 parts 1N hydrochloric acid. The solution is adjusted to pH 6.4 by the addition of sodium hydroxide solution and extracted with chloroform. The chloroform is removed by distillation to yield 43 parts of 2-dimethylamino-4,5-diemthyl-6-hydroxypyrimidine, analysing as 90% strength.

EXAMPLE 6

38.3 Parts of 2-ethylamino-4-hdroxy-6-methylpyrimidine, 5 parts of zinc acetate and 7 parts of a 50% aqueous paste of 3% palladium on carbon are stirred in 250 parts of acetic acid in a closed container. Hydrogen is passed into the reaction vessel to a pressure of 3 bar and the temperature is raised to 100°C. 20.4 Parts of n-butyraldehyde are added over 3½ hours maintaining a hydrogen pressure of 3 bar and temperature 96°–100°C. The reaction mixture is stirred under these conditions for a further 20 hours, and then cooled and the palladium on carbon catalyst removed by filtration. The filtrates are distilled under reduced pressure to remove water and acetic acid. The residue is stirred in 200 parts of water at 65°– 70°C and extracted with 200 parts of chloroform. The chloroform solution is extracted with 100 parts of water containing 22.5 parts of 35 % hydrochloric acid. The chloroform solution is evaporated to yield 14.6 parts of 5-butyl-2-ethylamino-4-hydroxy-6-methylpyrimidine, analysing at 77% strength.

EXAMPLE 7

76.25 Parts of 2-ethylamino-4-hydroxy-6-methylpyrimidine, 41 parts of n-butyraldehyde and 7 parts of a 50% aqueous paste of 3% palladium on carbon catalyst are stirred in 400 parts of n-butanol in a closed container. Hydrogen is passed into the reaction vessel to a pressure of 3 bar and the temperature is raised to 100°C. The reaction mixture is stirred under a hydrogen pressure of 3 bar and a temperature of 95°– 100°C for 18 hours, and then cooled and the palladium on carbon catalyst removed by filtration. The filtrates are distilled under reduced pressure to rermove butanol. The residue is stirred in 200 parts of water and the pH adjusted to 12 with sodium hydroxide solution. The suspension is filtered and the filtrates adjusted to pH 6.9 with hydrochloric acid. The suspension is filtered and the filter cake dried to yield 37.0 parts of crude 5-butyl-2-ethylamino-4-hydroxy-6-methylpyrimidine.

EXAMPLE 8

38.25 Parts of 2-ethylamino-4-hydroxy-6-methylpyrimidine, 21.6 parts of n-butyraldehyde and 7 parts of a 50% aqueous paste of 3% palladium on carbon catalyst are stirred in 200 parts of n-butanol in a closed container. Hydrogen is passed into the reaction vessel and the temperature is raised to 135°C. The reaction mixture is stirred at 120–135°C under 10 to 12 bar hydrogen pressure for 24 hours and then cooled and the palladium on carbon catalyst removed by filtration to yield a butanol solution containing 8 parts of 5-butyl-2-ethylamino-4-hydroxy-6-methylpyrimidine.

EXAMPLE 9

The procedure of Example 8 is repeated but in the presence of 0.43 parts of piperidine acetate to yield a butanol solution containing 11.3 parts of product.

EXAMPLE 10

38.25 Parts of 2-methylamino-4-6-methylpyrimidine, 5 parts of zinc acetate, 7 parts of a 50% aqueous paste of 3% palladium on carbon and 22 parts of n-butyraldehyde are stirred in 250 parts of 50% aqueous acetic acid in a closed container. Hydrogen is passed into the reaction vessel and the temperature is raised to 120°C. The reaction mixture is stirred at 100°–120°C under 10 to 12 bar hydrogen pressure for 5 hours, and then washed and the palladium on carbon catalyst removed by filtration. The filtrates are distilled under reduced pressure to remove water and acetic acid. The residue is stirred in 340 parts of water and 35 parts of 35% hydrochloric acid, filtered from extraneous matter and neutralised with sodium hydroxide liquor to yield a tacky precipitate which is extracted with 300 parts of chloroform and the water layer extracted twice more with 150 parts of chloroform. The combined chloroform extracts are distilled to yield 31.4 parts of a glass-like solid. 90 Parts by volume of acetone and 10 parts of water are added and refluxed for 1 hour. After the suspension is filtered and dired to yield 22.2 parts of 5-n-butyl-2-ethylamino-4-hydroxy-6-methyl pyrimidine analysing at 91% strength.

EXAMPLE 11

38.25 Parts of 2-ethylamino-4-hydroxy 6-methylpyrimidine, 5 parts of zinc acetate, 22 parts of butyraldehyde and 7 parts of a 50% aqueous paste of 3% palladium on carbon are stirred in 125 parts of acetic acid and 125 parts of ethyl acetate in a closed container. Hydrogen is passed into the reaction vessel and the temperature is raised to 112°C. The reaction mixture is stirred at 100°–112°C under 10 – 12 bar hydrogen pressure for 6 hours and then cooled and the palladium on carbon catalyst removed by filtration. The filtrates are distilled under reduced pressure to remove ethyl acetate and acetic acid. The residue is stirred at 30°C with 575 parts of 50% sodium hdyroxide solution, filtered from extraneous matter and neutralised with hydrochloric acid to pH 7. The suspension is filtered and the filter cake dried to yield 34.6 parts of crude product containing 16.4 parts of 5-n-butyl-2-ethylamino-4-hydroxy-6-methyl pyrimidine.

EXAMPLE 12

38.25 Parts of 2-dimethylamino-4-hydroxy-6-methylpyrimmidine, 5 parts of zinc acetate; 7 parts of a 50% aqueous paste of a 3% palladium on carbon catalyst and 22 parts of n-butyraldehyde are stirred in 125 parts of acetic acid and 125 parts of water in a closed container. Hydrogen is then passed into the reaction vessel and the temperature is raised to 108°C. The reaction mixture is stirred at 99°–114°C under 6–11 bar hydrogen pressure for 4 hours and then cooled and the palladium on carbon catalyst removed by filtration. The filtrates are distilled under reduced pressure to removed water and acetic acid. The residue is drowned into 200 parts of water. The resultant slurry is filtered, washed with water and dried to yield 38.7 parts of 5-n-butyl-2-dimethylamino-4-hydroxy-6-methylpyrimidine analysing at 96.0% strength.

EXAMPLE 13

38.25 Parts of 2-dimethylamino-4-hydroxy-6-methyl pyrimidine, 5 parts of zinc acetate and 7 parts of a 50% aqueous paste of 3% palladium on carbon catalyst are stirred in 180 parts of acetic acid and 180 parts of water in a closed container. Hydrogen is then passed into the reactor to a pressure of 1.5 bar. The temperature is raised to 103°C and the hydrogen pressure to 2.3 bar and 50 parts by volume of an 18% solution of formaldehyde in water are added at a uniform rate over 5 hours to the reaction mixture at 103°–110°C under 2 – 2.3 bar hydrogen pressure. After 1½ hours the reaction mixture is cooled and the palladium on carbon catalyst removed by filtration. The filtrates are distilled under reduced pressure to remove water and acetic acid. The residue is dissolved in 325 parts of 3% aqueous sodium hydroxide, filtered, neutralised with hydrochloric acid and extracted three times with 150 parts of chloroform. The chloroform solution is evaporated to dryness to yield 33 parts of pure 2-dimethylamino-4,5-dimethyl-6-hydroxy pyrimidine.

EXAMPLE 14

19.125 Parts of 2-dimethylamino-4-hydroxy-6-methylpyrimidine, 5 parts of zinc acetate and 7 parts of a 50% aqueous paste of 3% palladium on carbon catalyst are stirred in 320 parts of water and 37.5 parts of sulphuric acid in a closed container. Hydrogen is then passed into the reactor to a pressure of 1.5 bar. The temperature is raised to 94°C and the hydrogen pressure to 3 bar. 23 Parts of an 18% solution of formaldehyde in water are added at a uniform rate over 4½ hours at 93°–100°C under 2.7 – 3 bar hydrogen pressure. After a further 1½ hours the reaction mixture is cooled and the palladium carbon catalyst removed by filtration. The filtrates are neutralised with sodium hydroxide solution and extracted with 330 parts of chloroform. After screening, the chloroform layer is evaporated to yield 10.9 parts of 2-dimethylamine-4,5-dimethyl-6-hydroxy pyrimidine analysing at 90% strength.

EXAMPLE 15

19.15 Parts of 2-dimethylamine-4-hydroxy-6-methyl pyrimidine, 5 parts of hydrated magnesium acetate and 7 parts of a 50% aqueous paste of 3% palladium on carbon catalyst are stirred in 15.5 parts of acetic acid and 155 parts of water in a closed container. Hydrogen is then passed into the reactor to a pressure of 1.5 bar. The temperature is raised to 98°C and the hydrogen pressure to 3 bar. 22.5 Parts of an 18% solution is formaldehyde in water are added at a uniform rate over 4½ hours at 94°–100°C under 2.7 – 3 bar hydrogen pressure. After a further 1½ hours the reaction mixture is cooled and the palladium on carbon catalyst removed by filtration. The filtrates are distilled under reduced pressure to remove water and acetic acid, the residue extracted with 400 parts of 4% sodium hydroxide solution. After filtering the filtrates are neutralised with hydrochloric acid and extracted with chloroform. The chloroform extracts are distilled, finally under reduced pressure, to yield 8.1 parts of 2-dimethylamino-4,5-dimethyl-6-hydroxypyrimidine analysing at 98.9% strength.

EXAMPLE 16

The procedure of Example 13 is repeated but replacing the hydrated magnesium acetate by 5 parts of basic aluminium acetate to yield 7.7 parts of product analysing at 96.7% strength.

EXAMPLE 17

31.25 Parts of 2-amino-4-hydroxy-6-methylpyrimidine, 5 parts of zinc acetate, 39.6 parts of acetaldehyde and 7 parts of a 50% aqueous paste of 3% palladium on carbon catalyst are stirred in 66 parts of acetic acid and 180 parts of water and hydrogenated at 95°–100°C under 3 bar pressure for 6 hours. The reaction mixture is cooled and filtered to remove the palladium on carbon. The filtrates are distilled under reduced pressure to remove acetic acid and water and the residue dissolved in 100 parts of 4% hydrochloric acid. The solution is neutralised with sodium hydroxide and the precipitate collected by filtration and washed with water and 300 parts of chloroform to give 33.6 parts of product containing 43% of 2-amino-5-ethyl-4-hydroxy-6-methylpyrimidine and 7.5% of 2-amino-4-hydroxy-6-methylpyrimidine. The chloroform washings on evaporation yield 0.6 parts of a product of which the major component is 5-ethyl-2-ethylamino-4-hydroxy-6-methylpyrimidine.

EXAMPLE 18

The procedure of Example 17 is repeated but using 13.2 parts of acetaldehyde at a temperature of 100 – 102 under a pressure of 10 – 13 bar. Neutralisation of the hydrochloric acid solution afforded immediately 16.9 parts of product and, on standing, a further 4.6 parts of product. The first product contained 33% of 2-amino-5-ethyl-4-hydroxy-6-methylpyrimidine, and in lesser proportion 2-amino-4-hydroxy-6-methylpyrimidine and 5-ethyl-2-ethylamino-4-hydroxy-6-methylpyrimidine. The second product contained as major component 2-amino-5-ethyl-4-hydroxy-6-methylpyrimidine.

We claim:

1. A process for the manufacture of 2-amino-2-alkylamino- or 2-dialkylamino-4-hydroxy-5-alkyl-pyrimidines comprising the step of reacting 2-amino-, 2-alkylamino- or 2-dialkylamino-4-hydroxy-pyrimidine wherein the alkyl group or groups on the 2-amino group have not more than six carbon atoms with an aldehyde of the formula R.CHO wherein R is a hydrogen atom, alkyl having not more than five carbon atoms, alkenyl of 2 to 4 carbon atoms or phenyl in presence of hydrogen and a supported palladium hydrogenation cataylst.

2. A process as claimed in claim 1 wherein the 6-position in the pyrimidine ring is substituted by a methyl group.

3. A process as claimed in claim 1 in which there is additionally present a metal salt selected from the group consisting of zinc acetate, zinc chloride, magnesium acetate, aluminum acetate, lithium acetate, nickel chloride, nickel acetate and thallium acetate, or an acid selected from the group consisting of acetic acid, formic acid and sulphuric acid, or an acetate salt of an amine selected from the group consisting of piperidine, diethylamine and pyridine.

4. A process as claimed in claim 1 which is carried out in a water-miscible solvent.

5. A process as claimed in claim 1 wherein the process is carried out at a temperature from 80° to 120°C.

6. A process as claimed in claim 1 wherein the hydrogenation is at superatmospheric pressure.

7. A process as claimed in claim 1 wherein the aldehyde is added gradually to the other reactants at reaction temperature.

8. A process as claimed in claim 1 wherein the amount of aldehyde is from 1 to 2 molar proportions of the amount of the pyrimidine.

* * * * *